United States Patent [19]

Zennaro et al.

[11] Patent Number: 6,075,062

[45] Date of Patent: Jun. 13, 2000

[54] CATALYTIC COMPOSITION SUITABLE FOR THE FISCHER-TROPSCH PROCESS

[75] Inventors: Roberto Zennaro; Andrea Gusso, both of Venice, Italy; Patrick Chaumette, Bougival; Magalie Roy, Rueil-Malmaison, both of France

[73] Assignees: Agip Petroli S.p.A.; Eni S.p.A., both of Rome, Italy; Institut Francais de Petrole, Rueil-Malmaison, France

[21] Appl. No.: 09/147,762

[22] PCT Filed: Jun. 26, 1998

[86] PCT No.: PCT/EP98/04035

§ 371 Date: Mar. 23, 1999

§ 102(e) Date: Mar. 23, 1999

[87] PCT Pub. No.: WO99/01218

PCT Pub. Date: Jan. 14, 1999

[30] Foreign Application Priority Data

Jul. 3, 1997 [IT] Italy ................................. MI97A1574

[51] Int. Cl.⁷ ............................. C07C 27/00; B01J 23/16; B01J 23/20; B01J 21/14; B01J 23/40

[52] U.S. Cl. .......................... 518/715; 518/700; 502/353; 502/354; 502/246; 502/260; 502/326

[58] Field of Search ..................................... 518/700, 715; 502/353, 354, 246, 260, 326

[56] References Cited

U.S. PATENT DOCUMENTS

| | | | |
|---|---|---|---|
| 4,088,671 | 5/1978 | Kobylinski et al. | 260/449.6 |
| 4,206,135 | 6/1980 | Kugler et al. | 260/449.6 |
| 4,328,158 | 5/1982 | Innes et al. | 54/258 |
| 4,738,948 | 4/1988 | Iglesia et al. | 502/326 |
| 5,397,806 | 3/1995 | Soled et al. | 518/715 |
| 5,559,065 | 9/1996 | Lauth et al. | 502/5 |

*Primary Examiner*—Johann Richter
*Assistant Examiner*—J. Parsa
*Attorney, Agent, or Firm*—Oblon, Spivak, McClelland, Maier & Neustadt, P.C.

[57] ABSTRACT

A catalyst composition containing cobalt and tantalum on an inert carrier, and having utility in Fischer-Tropsch syntheses.

8 Claims, No Drawings

CATALYTIC COMPOSITION SUITABLE FOR THE FISCHER-TROPSCH PROCESS

The present invention relates to a catalytic composition suitable for the preparation reaction of hydrocarbons by means of the so-called Fischer-Tropsch synthesis; it also relates to the catalytic process for the preparation of hydrocarbons for which it is used.

More specifically, the present invention relates to a new catalytic composition for the production of hydrocarbons by means of the Fischer-Tropsch synthesis containing Cobalt and promoted by Tantalum, this composition being obtained by reacting derivatives of the above elements in the presence of a suitable carrier, as specified in more detail hereunder.

The selection of cobalt as main constituent of the active phase is due to the fact that this favours the formation of saturated linear hydrocarbons with a high molecular weight minimizing the formation of oxygenated and olefinic compounds, contrary to the well-known catalytic systems based on iron.

The known art cites numerous examples of catalysts based on cobalt used for the synthesis of paraffinic products with various distributions.

Since the first works of Fischer in 1932 (H. H Storch, N. Golumbic, R. B. Anderson, "The Fischer Tropsch and Related Synthesis", John Wiley & son, Inc., New York, 1951)—which described the development of a $Co/ThO_2/MgO$ system supported on kieselguhr—until today, the patented systems based on cobalt are essentially the following: $Co/Mg/ThO_2$ supported on kieselguhr (1954, Reinpruessen A. G.), Co/MgO supported on bentonite (1958, M. W. Kellog), Co/Th/Mg (1959, Rurchemie), Co/Th supported on silica-gel (1960, Esso Res.& Eng.), Co/Mg/Zr/Kieselguhr (1968, SU-A-660.324, Zelinskii INST.), Co/Ru/Keiselguhr (1976, U.S. Pat. No. 4,088,671 GULF), $Co/Zr/SiO_2$ (1980, GB-A-2.073.237, Shell), Co/Ru supported on titanium (1988, U.S. Pat. No. 4,738,948 Exxon), Co/Re/REO,K supported on alumina (1988, EP-A-313.375, Statoil), $Co/Mo,W/K,Na/SiO_2$ (1991, GB-A-2.258.414, IFP), $Co/Ru/Cu/K,Sr/SiO_2$ (1993, EP-A-581.619, IFP).

The effect of promoters on the system based on cobalt, from what is described in literature, is multiple; however it can be subdivided into various groups in relation to the function of the promoter (B. Jager, R. Espinoza in Catalysis Today 23, 1995, 21–22).

For example, promoters such as K, Na, Mg, Sr, Cu, Mo, W and metals of group VIII essentially increase the activity. Ru, Zr, rare-earth oxides (REO), Ti increase the selectivity to hydrocarbons with a high molecular weight. Ru, REO, Re, Hf, Ce, U, Th favour the regenerability of the catalyst.

Among the various promoters, ruthenium, alone or together with other elements, is certainly the most widely used.

The recent evolution of catalytic systems for the synthesis of hydrocarbons has led to the identification of various promoters to be coupled with cobalt in order to increase both the activity of these systems in terms of conversion of the reagents and also the selectivity to linear hydrocarbons with a high molecular weight. This evolution has taken place mainly in the last twenty years. The increase in price of crude oil in the 70s' provided the incentive for exploring other ways of producing liquid fuels and chemicals, among which the possibility of transforming synthesis gases into hydrocarbon products with a high molecular weight by means of the Fischer-Tropsch synthesis.

As far as the Fischer-Tropsch synthesis is concerned, this can refer to the hydrogenation process of carbon monoxide to produce higher hydrocarbons and oxygenated molecules with a prevalently linear chain. The reaction takes place in the presence of a mixture of hydrogen and carbon monoxide with or without carbon dioxide (so-called synthesis gas) at temperatures lower than 350° C. and at pressures of between 1 and 100 atm.

The wide range of catalysts and their modifications described in the known art and the wide range of operating conditions for the reduction reaction of carbon monoxide with hydrogen allows a considerable flexibility in the selectivity of the products, ranging from methane to heavy waxes with alcohols and olefins as by-products. The distribution of the products can be explained by the known growth mechanism obtained by a polymerization kinetics and processed by Anderson Shultz and Flory (P. Biloen, W. M. H. Sachtler, Advance in Catalysis, Vol. 30, pages 169–171, Academic Press, New York, 1981; R. B. Anderson, Catalysis, Vol. IV, P. H. Emmett ed., Reinhold, New York, 1956). In accordance with this model, the attempt to restrict the range of products in order to maximize for example the $C_5-C_{11}$ fraction (gasoline-range) results in selectivities to methane and the $C_2-C_4$ fraction of more than 40%. In addition the products obtained are essentially paraffins with a linear chain and olefins with a low octane number. The only possibility of deviating from the nature imposed by the Fischer-Tropsch polymerization kinetics is to identify catalytic systems which do not adhere to this kinetics mechanism. Typical examples are systems developed by Mobil which substantially couple the properties of the Fischer-Tropsch catalysts with the shape selectivity of zeolites (U.S. Pat. No. 4,157,338).

The possibility of maximizing the selectivity to heavy liquids and waxes (essentially paraffinic and without sulfur) offers on the other hand various advantages. In particular it is possible to minimize the selectivity to methane and the gas fraction. The subsequent treatment (e.g. hydrocracking, hydroisomerization) of this liquid-solid fraction of a paraffinic nature gives high quality medium distillates if compared with the medium distillates obtained from petroleum (Ball J., Gas. Matters, Apr. 27, 1989, pages 1–8). In this context the typical characteristic of catalysts based on cobalt to be highly selective in the production of higher paraffins is definitely advantageous. In addition, the use of catalysts with a reduced water gas shift activity, such as catalysts based on cobalt, implies a low selectivity to $CO_2$, contrary to the use of a traditional catalyst based on iron.

With respect to the productivity of catalysts based on cobalt, defined as weight of $C_{2+}$ hydrocarbons/weight of catalyst/time, from what is specified in literature, this seems to vary a great deal and to depend directly on the operating temperature. Increasing the operating temperature however is not a valid way of increasing the productivity to high quality liquid and solid hydrocarbons, as this would cause a consequent increase in the selectivity to methane and light gases. It is very important on the contrary from an economical point of view to maximize this productivity and to minimize at the same time the selectivity to methane. In other words it is important to maximize the production of high quality liquid and solid hydrocarbons ($C_{9+}$, $C_{22+}$).

In accordance with this important objective, it is necessary for the catalyst to be capable of combining a high productivity ($Prod.C_{2+}$) with a low selectivity to methane ($Sel.CH_4$).

A catalytic composition has now been found which, applied to the Fischer-Tropsch process, enables a high selectivity to $C_{2+}$ hydrocarbons and at the same time a low selectivity to methane.

In accordance with this, the present invention relates to a catalytic composition based on cobalt which allows conversions of the mixture of CO and $H_2$, known as synthesis gas, with or without $N_2$ and/or $CO_2$ and/or light gases ($C_1$–$C_4$), into saturated linear hydrocarbons containing from 77% to 88% by weight of $C_{5+}$ and from 24 to 31% by weight of $C_{9+}$ and with productivities into $C_{2+}$ of between 180 and 330 $gC_{2+}/Kg_{cat}/h$, maintaining a low selectivity to methane.

The catalytic composition of the present invention essentially consists of an inert carrier, cobalt in a quantity of from 1 to 50% by weight, preferably from 5 to 35% by weight, and tantalum in a quantity of from 0.05 to 5% by weight, preferably from 0.1 to 3% by weight, the complement to 100 consisting of the inert carrier, the cobalt and tantalum being present in metal form or in the form of a derivative.

The percentages of cobalt and tantalum are expressed as metals.

The cobalt and tantalum can be present as metal or as derivatives, in the latter case the oxide form being preferred.

As far as the inert carrier is concerned, this is preferably selected from at least one of the oxides of at least one of the following elements: silicon, aluminum, zinc, magnesium, titanium, zirconium, yttrium, tin and the relative mixtures.

The inert carrier which can be used is independent of the crystallographic structure of the above oxides. For example, aluminas can be used of any phase composition such as η, γ, δ, θ, α and the relative mixtures.

In the same way, when the inert carrier essentially consists of $TiO_2$, this can be in the form of rutile and/or anatase.

In the preferred embodiment, the inert carrier is selected from silica, γ alumina, δ alumina, titania and the relative mixtures, even more preferably from silica, γ alumina and the relative mixtures.

A further object of the present invention relates to a process for the preparation of the catalytic composition of the present invention which comprises:

a) a first deposition onto the inert carrier, preferably selected from silica and alumina, preferably via dry impregnation, of a cobalt salt; subsequent calcination to give a catalytic precursor; subsequent optional reduction and passivation of the calcined product;

b) deposition onto the catalytic precursor thus obtained of a derivative of tantalum, preferably via wet impregnation; subsequent calcination, optionally followed by reduction and passivation.

The cobalt and tantalum can be deposited according to various methods well known to experts in the field such as, for example, ion exchange, dry impregnation, wet impregnation; precipitation and coprecipitation, gelation and mechanical mixing.

In the case of cobalt however, the dry impregnation method is preferable. According to this technique, the material to be impregnated is put in contact with a volume of solution more or less equal to the pore volume. In step (a) it is preferable to use aqueous solutions of cobalt salts, such as halides, nitrate, oxalate, the complex formed with lactic acid and lactates, the complex formed with tartaric acid and tartrates, the complex formed with acetylacetonates. In the most preferred embodiment, cobalt nitrate is used.

In the case of tantalum on the other hand, this is preferably deposited by means of any impregnation technique, preferably wet impregnation. According to this technique, the inert carrier onto which the cobalt has been previously deposited, is completely covered with a solution of a derivative of tantalum, particularly tantalum alcoholates, such as ethoxide, propoxide, isopropoxide, methoxide. In the most preferred embodiment tantalum ethoxide dissolved in $C_1$–$C_5$ alcohols is used.

The inert carrier can be used partially or totally in the first phase. In the latter case all of the inert carrier is used in the preparation of the catalytic precursor in the first step. In the former case the inert carrier is used partially in the first step and partially in the second step.

In the preferred embodiment, the process of the present invention comprises the above steps a) and b) without the reduction and passivation phases.

As far as the calcination is concerned, this is a heating step at a temperature of between 400° C. and 750° C. to remove volatile substances and decompose the derivatives of cobalt and tantalum into oxides. The calcination is carried out in the presence of oxygen, air or other gases containing oxygen.

Before this step, the material can be subjected to drying, usually at reduced pressure at a temperature of between 80 and 120° C., with or without an inert gas. This operation has the purpose of eliminating (or strongly reducing) the possible solvents or water with which the material has been impregnated and gives dispersion homogeneity to the active phase.

With respect to the reduction, this is a step in which the material is treated with a reducing agent, preferably hydrogen or gas containing hydrogen. The reduction is carried out at a temperature of between about 250° C. and about 500° C., preferably from 300° to 450° C. for periods of time of between 0.5 and 24 hours, at pressures between atmospheric pressure and 40 bars.

As far as the passivation is concerned, this is carried out by treating the material with oxygen diluted with an inert gas, usually nitrogen. The temperature is preferably from 10 to 80° C. Using for example nitrogen containing 1–2% of oxygen with a stream of 2 liters/hour/$g_{cat}$, the passivation step can have a duration of from 1 to 5 hours at 25° C.

Some of the operating details relating to the preparation of the above catalytic compositions will however be more evident on reading the experimental examples below which, however, do not limit the catalytic compositions of the present invention.

A further object of the present invention relates to a process for the preparation of essentially linear, saturated hydrocarbons starting from synthesis gas (Fischer-Tropsch process) in the presence of the above catalytic composition.

The conversion of the synthesis gas into hydrocarbons takes place at a pressure normally between 1 and 100 bars, preferably from 10 to 75 bars, at a temperature generally within the range of 150° C. to 350° C., preferably from 170° C. to 300° C., even more preferably from 200° C. to 240° C. The hourly volumetric flow-rate is generally from 100 to 20000, preferably from 400 to 5000, volumes of synthesis gas per volume of catalyst and per hour. The ratio $H_2/CO$ in the synthesis gas is generally from 1:2 to 5:1, preferably from 1.2:1 to 2.5:1. Other gases, particularly $CO_2$ may also be present.

As is known to experts in the field, the preparation of the mixture of CO and $H_2$ can be carried out starting from natural gas prevalently consisting of methane. The oxidating agent can be oxygen or air. In the latter case it is evident that the mixture of synthesis gas will also contain a considerable quantity of nitrogen, which may or may not be eliminated of $CO/H_2$ before the Fischer-Tropsch reaction. The advantage of carrying out the Fischer-Tropsch reaction on mixtures in which nitrogen is still present, is evident.

The catalyst can be used in the form of fine powder (about 10–700 mm) or in the form of particles having an equivalent diameter of from 0.7 to 10 mm, respectively in the presence of a liquid phase (under the operating conditions) and a gaseous phase, or a gaseous phase. The liquid phase can consist of at least one hydrocarbon having at least 5, preferably at least 15, carbon atoms per molecule. In the preferred embodiment, the liquid phase essentially consists of the same reaction product.

Just to give an example, the catalysts of the present invention can be used in a fixed-bed reactor, fed in continuous with a mixture of CO and $H_2$ and operating under the following conditions:

| | |
|---|---|
| reaction temperature | 200–240° C. |
| reaction pressure | 20 bars |
| space velocity (GHSV) | 500–1500 $h^{-1}$ |
| $H_2$/CO mixture | 2/1 |

The reaction temperature is regulated in order to obtain a conversion higher than at least 45% of the volume of carbon monoxide fed (conv. CO %).

Following these conditions, the catalysts prepared as described in examples 1 to 11 were evaluated, using various carriers. The compositions are summarized in table 1.

The results of the reactivity tests are indicated in tables 2 to 4.

Catalysts Supported on $SiO_2$

COMPARATIVE EXAMPLE 1. Comparative Catalyst A (Co/Ru/$SiO_2$; 14% Co, 0.2% Ru).

A silica carrier (having a surface area of 520 $m^2$/g, a specific pore volume of 0.8 $m^3$/g, an average particle diameter of 0.5 mm, a specific weight of 0.42 g/ml) is dry impregnated with a nitric solution of Co(NO$_3$)$_2$.6H$_2$O at pH=2.5 in such quantities as to obtain a percentage of Co equal to 14% by weight referring to the total. The silica thus impregnated is dried at 120° C. for 16 hours, calcined at 400° C. in air for 4 hours, then treated in a stream of $H_2$ at a space velocity (GHSV) of 1000 $h^{-1}$, in a tubular reactor at 400° C. for 16 hours. The sample thus reduced is passivated in a mixture of (1%)$O_2$/(99%)$N_2$ with GHSV of 1000 $h^{-1}$ for 2 hours at room temperature.

A 7.5 $10^{-3}$ M solution is added to the monometallic sample, of Ru(NO$_3$)$_3$.xH$_2$O obtained with the following procedure: precipitation in the form of hydroxide at pH=7.2 of RuCl$_3$.xH$_2$O, subsequent elimination of the chlorides, resolubilization in conc. HNO$_3$ and dilution in CH$_3$COCH$_3$ in a ratio 1:250 v/v.

The acetone solution of ruthenium is added to the sample in such a quantity as to have 0.2% of Ru by weight referring to the total. The slurry is left under stirring for 2 hours and then dried under vacuum <10 mmHg at 50° C. A calcination phase in air follows at 350° C. for 4 hours and subsequently a reduction and passivation analogous to that described above.

COMPARATIVE EXAMPLE 2. Comparative Catalyst B (Co/Sc/$SiO_2$; 14% Co, 0.2% Sc).

For the preparation of catalyst B, a solution of Sc(NO$_3$)$_2$ $10^{-3}$ M in acetone is added to 50 g of the monometallic catalyst Co/$SiO_2$ prepared as described in example 1, in such a volume as to obtain a final weight percentage of Sc equal to 0.2%.

The suspension thus obtained is left under stirring for two hours and is then dried under vacuum at 50° C. The sample is calcined at 350° C. for 4 hours in air, reduced at 400° C. in $H_2$ for 16 hours with a GHSV of 1000 $h^{-1}$ and passivated in (1%)$O_2$/(99%)$N_2$ with a GHSV of 1000 $h^{-1}$ for 2 hours at room temperature.

EXAMPLE 3. Catalyst C1

(Co/Ta/$SiO_2$; 14% Co, 0.5% Ta).

A solution of Ta(EtO)$_5$ 0.01 M in ethanol is added to 50 g of the monometallic catalyst Co/$SiO_2$ prepared as described in example 1, in such a volume as to obtain a final weight percentage of tantalum equal to 0.5%.

The suspension thus obtained is left under stirring for two hours and is then dried under vacuum at 50° C.

The sample is calcined at 350° C. for 4 hours in air, reduced at 400° C. in $H_2$ for 16 hours with a GHSV of 1000 $h^{-1}$ and passivated in (1%) $O_2$/(99%)$N_2$ with a GHSV of 1000 $h^{-1}$ for 2 hours at room temperature.

EXAMPLE 3b. Catalyst C2

(Co/Ta/$SiO_2$; 14% Co, 0.2% Ta).

The catalyst C2 is prepared analogously to what is described in example 3.

EXAMPLE 4. Catalyst D (Co/Ta/$SiO_2$; 14% Co, 0.5% Ta).

A silica carrier (having a surface area of 520 $m^2$/g, a specific pore volume of 0.8 $m^3$/g, an average particle diameter of 0.5 mm, a specific weight of 0.42 g/ml) is dry impregnated with a nitric solution of Co(NO$_3$)$_2$.6H$_2$O at pH=2.5 in such quantities as to obtain a percentage of Co equal to 14% by weight referring to the total. The silica thus impregnated is dried at 120° C. for 16 hours and calcined at 400° C. in air for 4 hours. A solution of Ta(EtO)$_5$ 0.01 M in ethanol is added to the monometallic sample Co/$SiO_2$ in such a volume as to obtain a final weight percentage of tantalum equal to 0.5%.

The suspension thus obtained is left under stirring for two hours and is then dried under vacuum at 50° C.

A calcination phase in air follows at 350° C. for 4 hours.

Catalyst Supported on $TiO_2$

COMPARATIVE EXAMPLE 5. Comparative Catalyst E (Co/Ru/$TiO_2$; 12% Co, 0.2% Ru).

Following the procedure described in example 1, comparative catalyst E is prepared completely similar to catalyst A but having $TiO_2$ as carrier instead of $SiO_2$. In this case the $TiO_2$ had a surface area of 25 $m^2$/g, a specific pore volume of 0.31 $cm^3$/g and a content of rutile equal to 81%.

COMPARATIVE EXAMPLE 6. Comparative Catalyst F (Co/Sc/$TiO_2$; 12% Co, 0.2% Sc)

Catalyst F is prepared analogously to what is described for the preparation of catalyst B.

EXAMPLE 7. Catalyst G (Co/Ta/$TiO_2$; 12% Co, 0.5% Ta).

Following the procedure described in example 4, catalyst G is prepared, consisting of the carrier based on titania. In this case the $TiO_2$ had a surface area of 25 $m^2$/g, a specific pore volume of 0.31 $cm^3$/g and a content of rutile equal to 81%.

Catalysts Supported on SiO$_2$—TiO$_2$

EXAMPLE 8. Catalyst H
(Co/Ta/[Si—Ti]; 15% Co, 0.5% Ta).

A silica carrier (having a surface area of 480 m$^2$/g, a specific pore volume of 0.8 m$^3$/g, a particle size of between 75 and 150 μm, a specific weight of 0.55 g/ml, average pore radius of 35 Å) previously dried at 150° C. for 8 hours is suspended, under a nitrogen atmosphere, in anhydrified n-hexane, 6 ml/g SiO$_2$. A solution of Ti(i-PrO)$_4$ 0.2 M is added to the slurry in such a quantity as to have about 7.0% of Ti; the mixture is left under stirring for 16 hours and is then dried under vacuum with a pressure of <10 mmHg and a temperature of 50° C. The sample thus obtained is calcined in a nitrogen atmosphere at 400° C. for 4 hours and subsequently calcined in air at 600° C. for a further 4 hours.

Catalyst H is prepared with the mixed carrier thus obtained, consisting of 7.1% of titanium of which about 25% in crystalline form (50% rutile, 50% anatase) and a surface area of 440 m$^2$/g, analogously to what is described in example 4.

Catalysts Supported on Al$_2$O$_3$

EXAMPLE 9. Catalyst I
(Co/Ta/Al$_2$O$_3$; 14% Co, 0.5% Ta).

Catalyst I is prepared analogously to what is described in example 4, with an alumina carrier (crystalline phase 100% gamma, surface area of 175 m$^2$/g, specific pore volume 0.5 m$^3$/g, average pore radius 40 Å, particle size between 20–150 μm, specific weight of 0.86 g/ml).

EXAMPLE 10. Catalyst L
(Co/Ta/Al$_2$O$_3$; 12% Co, 0.5% Ta).

Catalyst L is prepared analogously to what is described in example 4, with an alumina carrier (crystalline phase 50% γ and 50% δ, surface area of 137 m$^2$/g, specific pore volume 0.46 m$^3$/g, average pore radius 45 Å, particle size between 20–120 μm, specific weight of 0.69 g/ml).

CATALYTIC TESTS

EXAMPLE 11
Evaluation of the Catalytic Activity of Catalysts Supported on Silica.

The catalyst (A, B, C, D according to examples 1–4) is formed in particles having a diameter of between 0.35 and 0.85 mm and is subsequently diluted with an inert carrier, silicon carbide, having the same particle size as the catalyst and in a volumetric ratio catalyst/inert carrier equal to 1:2. The catalyst thus diluted is then charged into a tubular reactor and subjected to an activation procedure in a stream of hydrogen (2000 Nl/h·l$_{cat}$) and nitrogen (1000 Nl/h·l$_{cat}$), at a temperature of between 350–400° C. and a pressure of 1 bar for 16 hours. The temperature is then lowered to 180° C., the volumetric flow-rate of hydrogen and nitrogen is modified (333–1000 Nl/h·l$_{cat}$) and (5000–15000 Nl/h·l$_{cat}$) respectively, the system is pressurized to 20 bars and carbon monoxide is then introduced (116.5–500 Nl/h·l$_{cat}$) to obtain a volumetric ratio H$_2$/CO equal to 2.

The flow-rate of nitrogen in the starting phase of the reaction is progressively lowered until complete elimination according to the following sequence (the lower flow-rates refer to tests with GHSV=500 h$^{-1}$, the higher flow-rates to GHSV=1500 h$^{-1}$):

| time (hrs) | flow-rate H$_2$ (Nl/h · 1$_{cat}$) | flow-rate CO (Nl/h · 1$_{cat}$) | flow-rate N$_2$ (Nl/h · 1$_{cat}$) |
|---|---|---|---|
| 0 | 333–1000 | 166.5–500 | 5000–15000 |
| 1 | 333–1000 | 166.5–500 | 3750–11250 |
| 2 | 333–1000 | 166.5–500 | 2500–7500 |
| 3 | 333–1000 | 166.5–500 | 1250–3750 |
| 4 | 333–1000 | 166.5–500 | 0 |

At the end of the starting phase, the reaction temperature is regulated so as to obtain a conversion of carbon monoxide with respect to the volume fed (conv. CO %) of less than 20% for at least 48 hours, then in the following 48 hours the temperature is gradually increased until a minimum CO conversion value of 45% is reached, without however exceeding the reaction temperature of 240° C., in order to minimize the production of methane as well as the light gaseous fractions (C$_2$–C$_4$).

As indicated in table 2 for comparative catalyst A, in order to reach conversions of CO higher than the limit of 45%, it is necessary to increase the reaction temperature (from 200° C. to 240° C.) with an increase in the volumetric flow-rates of the mixture H$_2$—CO (GHSV from 500 h$^{-1}$ to 1500 h$^{-1}$). As a result the selectivity to methane is favoured (from 7.8% to 29.7%), expressed as percentage referring to the total carbon present in the products (C %), to the total disadvantage of the selectivities to higher hydrocarbons (Sel.C$_{22+}$ from 15.4% to 3.2%, Sel.C$_{9+}$ from 66.9% to 48.8%), expressed as percentage referring to the total weight of the whole hydrocarbon fraction produced (weight %).

With respect to comparative catalyst B, promoted with scandium, using a total volumetric flow-rate equal to 1500 h$^{-1}$ and a reaction temperature of 218° C., an hourly weight productivity to hydrocarbons with more than two carbon atoms (C$_{2+}$) equal to 273 g/kg/h and selectivities to C$_{22+}$ of 14.2% are obtained. In general the catalytic performances of catalyst B can be considered as being higher than those of catalyst A.

Catalysts C1, C2 and D of the present invention, containing Tantalum, are subjected to an analogous catalytic test. As indicated in table 2, with a total volume flow-rate (GHSV) equal to 1500 h$^{-1}$ and a reaction temperature of 220° C., for catalysts C1 and C2, prepared with the same procedure as catalysts A and B, CO conversions are obtained of 60.3% and 69.3% respectively, productivities to C$_{2+}$ of more than 315 gC$_{2+}$/Kg$_{cat}$/h, selectivities to methane of less than 10%, selectivities to C$_{22+}$ higher hydrocarbons of about 24%, selectivities to C$_{9+}$ hydrocarbons of between 65.6% and 71.3% and finally selectivities to C$_{5+}$ of more than 81%.

These performances are better than those obtained with comparative catalysts A and B, especially for the higher productivities, selectivities to higher hydrocarbons and lower selectivities to methane and light gas fractions (C$_2$–C$_4$).

With respect to catalyst D, synthesized with the procedure described in example 4, the catalytic performances of the Co/Ta system are further improved compared to the comparative catalysts: Co conversions of 71.0%, productivities to C$_{2+}$ of 330 gC$_{2+}$/Kg$_{cat}$/h, selectivities to methane of 8.4%, selectivities to $C_{22+}$ higher hydrocarbons of 29.1%, selectivities to $C_{9+}$ hydrocarbons of 78.4% and finally selectivities to $C_{5+}$ of 83.5%.

EXAMPLE 12
Evaluation of the Catalytic Activity of Catalysts Supported on Titania As indicated in table 3, also in this case the comparison between the reference catalysts promoted with ruthenium (cat. E) or scandium (cat. F) and the catalyst promoted without the intermediate reduction and passivation phase (example 3), shows an increase in the CO conversion, total hydrocarbon productivity and selectivity to higher hydrocarbons, maintaining a low selectivity to methane (CO conv.=70.0%, Prod.$C_{2+}$=172 g/$Kg_{cat}$/h, $C_{22+}$=32.9%, $CH_4$= 7.6%).

EXAMPLE 13
Evaluation of the Catalytic Activity of Catalysts Supported on Silica/Titania and Alumina.

The catalytic composition Co/Ta supported on other materials such as the mixed carrier silica-titania and alumina with a different phasic composition showed interesting catalytic performances at reaction temperatures of between 209 and 218° C. and total volumetric flow-rates of 1500 $h^{-1}$.

As indicated in table 4, the conversions obtained are higher than 57% (CO conv.=65.8÷57.1%), productivities to $C_{2+}$ higher than 180 g/kg/h (Prod.$C_{2+}$: 183.1÷260.1 g/kg/h), selectivities to hydrocarbons $C_{22+}$ higher than 23% (Sel.$C_{22+}$: 23.2÷28.3).

The data of table 5 show the possibility of using synthesis gas diluted with nitrogen.

TABLE 1

| Example | Cat. | % Co | % X | X | Carrier |
|---|---|---|---|---|---|
| Comp. 1 | A | 14 | 0.2 | Ru | $SiO_2$ |
| Comp. 2 | E | 14 | 0.2 | Sc | $SiO_2$ |
| 3 | C1 | 14 | 0.5 | Ta | $SiO_2$ |
| 3b | C2 | 14 | 0.2 | Ta | $SiO_2$ |
| 4 | D | 14 | 0.5 | Ta | $SiO_2$ |
| Comp. 5 | E | 12 | 0.2 | Ru | $TiO_2$ |
| Comp. 6 | F | 12 | 0.2 | Sc | $TiO_2$ |
| 7 | G | 12 | 0.5 | Ta | $TiO_2$ |
| 8 | H | 12 | 0.5 | Ta | $SiO_2$-$TiO_2$ |
| 9 | I | 14 | 0.5 | Ta | $\gamma$-$Al_2O_3$ |
| 10 | L | 12 | 0.5 | Ta | $\gamma$, $\delta$-$Al_2O_3$ |

TABLE 2

Example 11
Catalysts supported on Silica

| Catalyst | A | A | A | B | C1 | C2 | D |
|---|---|---|---|---|---|---|---|
| React. temp. (° C.) | 200 | 220 | 240 | 218 | 212 | 222 | 220 |
| GHSV $h^{-1}$ | 500 | 1.000 | 1.500 | 1.500 | 1.500 | 1.500 | 1.500 |
| CO conv. (%) | 48.5 | 51.3 | 47.1 | 57.6 | 60.3 | 69.3 | 71 |
| Prod. $C_{2+}$ (g/Kg/h) | 81.4 | 149 | 183.5 | 272.6 | 315.3 | 326.2 | 330.1 |
| $CH_4$ (C %) | 7.8 | 18.8 | 29.7 | 10.3 | 7.1 | 9.5 | 8.4 |
| $CO_2$ (C %) | 0.3 | 1.8 | 2.2 | 0.1 | 0.9 | 0.5 | 0.6 |
| $C_1$–$C_4$ (wt %) | 13.5 | 32.7 | 49 | 17.3 | 15.9 | 19 | 16.5 |
| $C_{22+}$ (wt %) | 15.4 | 14.1 | 3.2 | 14.2 | 23.9 | 24.7 | 29.1 |
| $C_{9+}$ (wt %) | 66.9 | 64.1 | 48.8 | — | 65.6 | 71.3 | 78.4 |
| $C_{5+}$ (wt %) | 86.5 | 67.3 | 51 | 82.8 | 84.1 | 81.1 | 83.5 |

TABLE 3

Example 12
Catalysts supported on Titania

| Catalyst | E | F | G |
|---|---|---|---|
| React. temp. (° C.) | 228 | 228 | 214 |
| GHSV $h^{-1}$ | 1.500 | 1.500 | 1.500 |
| CO conv. (%) | 54.3 | 61.6 | 70 |
| Prod. $C_{2+}$ (g/Kg/h) | 144.6 | 152.3 | 171.7 |
| $CH_4$ (C %) | 7.6 | 13.3 | 7.6 |
| $CO_2$ (C %) | 0.1 | 0.1 | 0.1 |
| $C_1$–$C_4$ (wt %) | 12.6 | 19 | 12.1 |
| $C_{22+}$ (wt %) | 21.9 | 17.6 | 32.9 |
| $C_{5+}$ (wt %) | 87.4 | 81 | 87.9 |

TABLE 4

Catalysts supported on Si-Ti and alumina
Example 13
Catalysts supported on Si-Ti and alumina

| Catalyst | H | I | L |
|---|---|---|---|
| React. temp. (° C.) | 209 | 214 | 218 |
| GHSV $h^{-1}$ | 1.500 | 1.500 | 1.500 |
| CO conv. (%) | 65.8 | 59 | 57.1 |
| Prod. $C_{2+}$ (g/Kg/h) | 260.1 | 183.1 | 196.2 |
| $CH_4$ (C %) | 10.5 | 9.8 | 8.5 |
| $CO_2$ (C %) | 0.4 | 0.5 | 0.5 |
| $C_1$–$C_4$ (wt %) | 19.4 | 22.4 | 17.6 |
| $C_{22+}$ (wt %) | 23.2 | 28.3 | 24.8 |
| $C_{9+}$ (wt %) | 68.2 | 65.5 | 70.4 |
| $C_{5+}$ (wt %) | 80.6 | 77.6 | 82.4 |

TABLE 5

Test in-the presence of Nitrogen

| Catalyst | I | I |
|---|---|---|
| React. temp. (° C.) | 226 | 235 |
| GHSV $h^{-1}$ | 1.500 | 1.500 |
| Content & $N_2$ | 20.6 | 20.6 |
| CO conv. (%) | 44 | 65.4 |
| Prod. $C_{2+}$ (g/Kg/h) | 120.4 | 173.5 |
| $CH_4$ (C %) | 15 | 13.4 |
| $CO_2$ (C %) | 0.4 | 0.9 |
| $C_1$–$C_4$ (wt %) | 27 | 28 |
| $C_{22+}$ (wt %) | 28.2 | 21.4 |
| $C_{9+}$ (wt %) | 59.1 | 62.6 |
| $C_{5+}$ (wt %) | 73 | 72 |

What is claimed is:

1. A catalytic composition consisting essentially of an inert carrier, cobalt in a quantity of from 1 to 50% by weight of the composition, and tantalum in a quantity of from 0.05 to 5% by weight of the composition, the cobalt and tantalum being present in metal form of in the form of a derivative, and wherein the inert carrier is selected from the group consisting of silica, γ-alumina, and mixtures thereof.

2. The catalytic composition according to claim 1, wherein the cobalt is present in a quantity of from 5 to 35% by weight and the tantalum from 0.1 to 3% by weight.

3. A process for the preparation of the catalytic composition according to claim 1 which comprises:

a) a first deposition onto the insert carrier, of a cobalt salt; subsequent calcination to give a catalytic precursor; subsequent optional reduction and passivation of the calcined product;

b) deposition onto the catalytic precursor thus obtained of a derivative of tantalum; subsequent calcination, optionally followed by reduction and passivation.

4. The process according to claim 3, wherein the cobalt is deposited onto the inert carrier via dry impregnation.

5. The process according to claim 3, wherein the tantalum is deposited via wet impregnation.

6. A process for the synthesis of essentially linear and saturated hydrocarbons starting from synthesis gas comprising CO and $H_2$, optionally diluted with nitrogen, comprising reacting the optionally diluted synthesis gas in the presence of the catalyst according to claim 1, at a pressure of between 1 and 100 bars, a temperature of between 150° C. and 350° C., the molar ratio $H_2/CO$ in the synthesis gas being from 1:2 to 5:1.

7. The process according to claim 6, wherein the reaction temperature is between 170° C. and 300° C., the pressure between 10 and 75 bars, the ratio $H_2/CO$ in the synthesis gas being from 1.2:1 to 2.5:1.

8. The process according to claim 7, wherein the temperature is from 200° C. to 240° C.

* * * * *